United States Patent

Atkinson et al.

[11] Patent Number: 5,907,407
[45] Date of Patent: May 25, 1999

[54] ILS SENSORS FOR ALCOHOL DETECTION WITHIN VEHICLES

[75] Inventors: George H. Atkinson; Markus A. Wolperdinger; Jeffrey S. Pilgrim, all of Tucson, Ariz.

[73] Assignee: Innovative Lasers Corporation, Tucson, Ariz.

[21] Appl. No.: 09/131,437

[22] Filed: Aug. 10, 1998

[51] Int. Cl.$^6$ .................................................. G01N 21/00
[52] U.S. Cl. ........................ 356/437; 356/442; 356/439; 356/326
[58] Field of Search ................................. 356/437, 442, 356/439, 326

[56] References Cited

U.S. PATENT DOCUMENTS

| | | | |
|---|---|---|---|
| 5,689,334 | 11/1997 | Atkinson | 356/437 X |
| 5,723,864 | 3/1998 | Atkinson | 356/328 X |
| 5,742,054 | 4/1998 | Atkinson | 356/439 X |
| 5,747,807 | 5/1998 | Atkinson | 356/328 X |

Primary Examiner—Robert Kim
Assistant Examiner—Reginald A. Ratliff
Attorney, Agent, or Firm—Benman & Collins

[57] ABSTRACT

On-board ILS ethyl alcohol sensors based on intracavity laser spectroscopy (ILS) are provided for detecting the presence of ethyl alcohol vapors in a vehicle. The sensor comprises: (a) a laser comprising a gain medium having two opposed facets within a laser resonator and functioning as an intracavity spectroscopic device having a first end and a second end, the first end operatively associated with a partially reflecting (i.e., partially transmitting) surface; (b) a reflective or dispersive optical element (e.g., a mirror or a diffraction grating) operatively associated with the second end to define a broadband wavelength laser resonator between the optical element and the first end and to thereby define an external cavity region between at least one facet of the gain medium and either the first end or the second end or both ends; (c) the external cavity region being exposed to air in the cabin of the vehicle to enable any ethyl alcohol molecules to enter thereinto; (d) a detector spaced from the first end; (e) appropriate electronics for measuring and analyzing the detector signal; (f) a housing for containing at least the laser, the partially reflecting surface, and the optical element, the housing being configured to prevent escape of stray radiation into the cab and to permit air from the cab to continuously circulate through the external cavity region for analysis; and (g) means for driving the laser (e.g., electrical or optical). A method is provided for measuring concentration of ethyl alcohol vapors in a vehicle employing the on-board sensor. The method comprises: (1) sensing any ethyl alcohol vapors in the cab by the on-board sensor; and (2) providing a signal indicative of presence of any alcohol vapors.

20 Claims, 6 Drawing Sheets

ILS SENSORS FOR ALCOHOL DETECTION WITHIN VEHICLES

TECHNICAL FIELD

The present invention relates generally to sensors for detecting ethyl alcohol vapors, and, more particularly, to on-board ethyl alcohol sensors employing intracavity laser spectroscopy (ILS) to detect the presence of alcohol in intoxicated drivers in vehicles.

BACKGROUND ART

Detecting alcohol-impaired drivers has gained a high level of importance during the last decade. In most cases, the reason to identify alcohol-impaired individuals participating in public traffic is motivated by safety issues and legal implications caused by these individuals operating cars, machinery or other equipment. Safety and legal issues are both very important in the context of a mobile society heavily relying on motorized vehicles for transportation. Financial implications for individuals or groups of the society resulting from accidents are considerable. Recognizing the importance of these facts, the abatement of alcohol-related accidents has been identified as prime target by the U.S. government.

Conventional technology utilized for alcohol (also referred to herein as ethanol or ethyl alcohol, $CH_3CH_2OH$) detection in traffic and traffic related situations relies on two different approaches:

1. Screening for blood alcohol is used to determine whether an individual's blood alcohol content (BAC) is below or above a certain threshold value. In most cases, screening is done by means of breath analysis to establish the breath alcohol content (BrAC). Conversion factors have been established to convert BrAC values into BAC values. The most commonly accepted conversion factor is 2100 (A. W. Jones, "Precision, Accuracy and Relevance of Breath Alcohol Measurements", *Modern Problems of Pharmacopsychiatry*, Vol. 11, pp. 65–78, 1976). Although breath analyzers are used frequently in traffic control situations, e.g., at sobriety checkpoints or for random screening of equipment operators, they only yield initial results to justify further evidential blood alcohol tests.

2. Evidential blood alcohol testing is the method of choice to establish legally-binding BAC values and, normally, is required after a positive breath alcohol test result. For the purpose of evidential alcohol tests, breath analysis with certified breath analyzers, chemical urine analysis, or blood sample analysis are most commonly employed. However, these methods, especially urine and blood tests, are time-consuming, require expensive equipment and trained operators and may necessitate medical supervision.

Both of the above approaches are based on technologies which can only be applied external to a vehicle and require the cooperation of tested individuals with authorities conducting the alcohol test. Besides these commonalities, both approaches share several significant shortcomings:

(a) Only selected vehicles can be tested for alcohol-impaired drivers due to logistical and personnel limitations, allowing a high percent rate of drivers under the influence to continue to drive.

(b) Vehicles with drivers suspected to be under the influence have to be stopped, necessitating costly sobriety checkpoints and follow-up examinations.

(c) Expensive equipment has to be setup and maintained at high cost.

(d) Human interaction is required, accounting for a variety of different problems, e.g., high personnel costs, risk of violent encounters, etc.

(e) Testing is sporadic and does not provide continuous monitoring of the driver's condition with respect to the ingestion of alcohol.

These facts lead to the conclusion, that (i) conventional technologies available to identify alcohol-impaired drivers are limited in their applicability and (ii) due to their conceptual shortcomings, these methods are even less suited to contribute to a significant further reduction of alcohol abuse in traffic as required by the government.

There are a number of technologies that are used for alcohol detection in gas samples. The following operational principles can be found in most commercial breath analyzers:

1. Fuel Cells: Fuel cell sensor devices are based on electrochemical reactions, in which alcohol in the gas phase is oxidized on a catalytic electrode surface to generate a quantitative electrical response. Sample gas is injected or drawn into the detector causing system response proportional to the alcohol concentration in the gas sample.

2. Semiconductors: Sensors of this type utilize small, heated (300° C.) beads of a transition metal oxide, across which a voltage is applied to produce a small standing current. The magnitude of this current is determined by the conductivity of the surface of the bead. Since the conductivity is affected by the amount of alcohol molecules adsorbed, it can be taken as a measure for the alcohol concentration in the gas sample.

3. Infrared Absorption: Absorption devices for breath sampling operate on the principle of infrared light being absorbed by alcohol molecules. The amount of light absorbed by the gas sample flowing though the sample cell can be taken as a measure of the alcohol content.

4. Gas Chromatography: This technique uses the ability of inorganic compounds to retain gas molecules on their surface in a characteristic way for different species. The retention time of alcohol in a separating column filled with the compound is used for its identification, the magnitude of detector response can be taken as a measure for the alcohol concentration in the gas sample.

5. Colorimetry: Devices based on this effect make use of the color change some chemicals display when reacting with alcohol. A gas sample is drawn into a small glass tube filled with a substrate containing an acidified solution of potassium dichromate. In the presence of alcohol, the color of the substrate changes from yellow to green. The length of the discolored portion of the tube can be taken as a measure for the alcohol concentration of the sample.

None of these devices has yet fulfilled the simultaneous requirements of fast response, high sensitivity, and continuous on-board monitoring in a moving vehicle. Thus, they are only utilized as the result of driver intervention by law enforcement personnel.

A new generation of small, highly-sensitive, on-board alcohol detectors would help to greatly reduce the number of alcohol-impaired drivers by preventing individuals under the influence from driving vehicles. These sensors, mounted within the cabin area of vehicles, would address the problem of driving under the influence before it even arises.

DISCLOSURE OF INVENTION

In accordance with the present invention, alcohol sensors based on intracavity laser spectroscopy (ILS) meet these requirements and provide the potential to extend alcohol detection beyond the performance available from the current, state-of-the-art detection technologies. An on-board ILS sensor for detecting the presence of ethyl alcohol vapors emitted by a driver in a cabin of a vehicle is provided that comprises:

(a) a laser comprising a gain medium having two opposed facets within a laser resonator and functioning as an intracavity spectroscopic device having a first end and a second end, the first end operatively associated with a partially reflecting (i.e., partially transmitting) surface;

(b) a reflective or dispersive optical element (e.g., a mirror or a diffraction grating) operatively associated with the second end to define a broadband wave-length laser resonator between the optical element and the first end and to thereby define an external cavity region between at least one facet of the gain medium and either the first end or the second end or both ends;

(c) the external cavity region being exposed to a sample of air representative of the air in the cabin of the vehicle to enable any ethyl alcohol molecules to enter thereinto;

(d) a detector spaced from the first end and providing an output detector signal;

(e) appropriate electronics for measuring and analyzing the detector signal;

(f) a housing for containing at least the laser, the partially reflecting surface, and the optical element, the housing being configured to prevent escape of stray radiation into the cabin and to permit air from the cabin to continuously circulate through the external cavity region for analysis; and (g) means for driving the laser (e.g., electrical or optical).

A focusing, expanding, or collimating intracavity optical element (e.g., a lens) to shape the beam may be placed in the external intracavity region.

A method is provided for measuring concentration of ethyl alcohol vapors in a vehicle employing the above-described on-board sensor. The method comprises:

(1) sensing any ethyl alcohol vapors in the vehicle by the on-board sensor;

(2) providing a signal indicative of presence of any ethyl alcohol vapors.

Other objects, features, and advantages of the present invention will become apparent upon consideration of the following detailed description and accompanying drawings, in which like reference designations represent like features throughout the FIGURES.

BRIEF DESCRIPTION OF THE DRAWINGS

The drawings referred to in this description should be understood as not being drawn to scale except if specifically noted.

BEST MODES FOR CARRYING OUT THE INVENTION

Reference is now made in detail to a specific embodiment of the present invention, which illustrates the best mode presently contemplated by the inventors for practicing the invention. Alternative embodiments are also briefly described as applicable.

In accordance with the present invention, an alternative concept to prior art approaches for on-board alcohol detection in traffic capitalizes on three important characteristics of the ILS technology: (i) high sensitivity; (ii) the ability to work with small volume gas samples, and (iii) continuous operation. This new concept derives from the installation of a small and inexpensive ILS alcohol sensor inside the vehicle that monitors the alcohol content of the air continuously through a small input port situated in front of the driver.

ILS alcohol sensors employed as on-board sensors respond within seconds to changes in alcohol levels, thereby permitting permanent alcohol detection in both standing and moving vehicles without interrupting the flow of traffic. An on-board alcohol sensor would also respond to a situation where alcohol is consumed in the vehicle.

Once alcohol has been detected inside the vehicle, there is a wide variety of options concerning how this information can be used. Drivers under the influence would not be able to start the vehicle (i.e., the ignition of the vehicle could be inhibited in the presence of alcohol above a set threshold value) or a signal could be sent out by the sensor to a remote detection unit outside of the vehicle. If desirable, feedback from the sensor could be available for vehicle occupants, allowing them to make a responsible decision whether to use the vehicle or abstain from driving.

One important aspect of the on-board ILS alcohol sensor concept is the fact that it could eliminate the need for conventional sobriety checkpoints. A readout of a car traveling normally on the road could be interrogated via a handheld "alcohol gun", or automatically at remote unmanned interrogation sites located at key locations. The identification of an alcohol-impaired driver could be radioed to a central location or the nearest patrol cars for action or using satellite communication for automated investigation of on-board sensors.

Not to be minimized with this new concept is the fact that the cooperation of the driver is not required in order to obtain a measurement of the alcohol concentrations. The vehicle does not have to slow down or drive through a special test fixture. All the driver must do is breathe normally.

The wavelength-laser energy combination utilized for the sensor was identified to be within the so-called "eye safe region" so as to present no potential danger to eyes and skin of people occupying the vehicle. Since the on-board ILS alcohol sensor is completely enclosing the laser beam and the radiation is contained within the sensor housing, its use totally obviates any laser radiation damage concerns.

In summary, ILS-based sensors for alcohol detection in vehicles are anticipated to significantly facilitate and improve alcohol vapor detection by obviating many of the difficulties encountered in conventional approaches. On-board ILS alcohol sensors have a great potential to significantly reduce alcohol related incidents in traffic and, therefore, eliminating the need for many "after the fact" methodologies currently used to establish BAC values if an accident has occurred.

The following list summarizes the most important advantages of on-board ILS alcohol sensors:

high sensitivity for alcohol vapor;
fast response of sensor (in seconds);
only small sample volumes required;
continuous, real time monitoring of alcohol vapor while vehicle is moving (no need to stop the vehicle to determine the presence of alcohol);
light weight, small and rugged sensor design;
all radiation contained physically, therefore, safe to human eyes and tissue;
low cost of ownership, low maintenance costs, due to simple design;
compatible with virtually every vehicle type;
feedback of sensor reading to driver possible, if desired;
remote, unmanned sensing of virtually every vehicle passing monitoring locations possible;
no driver cooperation or interaction between driver and police required;
alcohol detection in vehicles with windows either closed or opened (different sensitivity ranges may be utilized to address different degrees of dilution caused by open windows);
no need for sobriety checkpoints; and
cost reduction by investigation of suspect vehicles only.

The concept of optical ILS alcohol sensors, deployed inside vehicles and used as continuously operating on-board devices is described below. Important issues related to the functionality of the sensor as well as operational questions associated with sensor operation in vehicles are discussed in detail.

Optical on-board alcohol sensors, utilizing intracavity laser spectroscopy (ILS), can be envisioned as small, highly integrated devices. They are based on the principle of absorption enhancement inside a laser resonator taking advantage of high absorption gain achieved within small sample volumes. This approach has been successfully demonstrated by the inventors for different ILS laser configurations and for a wide variety of molecules; see, e.g., U.S. Pat. Nos. 5,689,334, issued Nov. 18, 1997; 5,723,864, issued Mar. 3, 1998; 5,742,054, issued Apr. 21, 1998; and 5,747,807, issued May 5, 1998, all to George H. Atkinson et al.

To develop and utilize ILS technology for small on-board alcohol sensors, a series of interrelated technical questions has to be addressed and resolved. These technical questions are:

What is the amount of alcohol generated by an alcohol-impaired driver in a vehicle under different conditions?
In which region of the optical spectrum can alcohol vapor be detected?
What is the minimum sensitivity an on-board alcohol sensor must achieve to allow for reliable alcohol detection?
What is the ILS laser design most suitable for small on-board alcohol sensors?
Are there any possible interferences with other airborne species present in the cabin?
What are possible safety hazards caused by the operation of on-board alcohol sensors in close proximity to vehicle occupants?

A key question concerning specifications for on-board alcohol sensors revolves around the concentration of alcohol molecules in a vehicle cabin generated by a driver under the influence.

According to the current law in many states, a person with 0.10 grams of alcohol in 100 $cm^3$ of blood is considered to be under the influence. Laws which would set the national standard of 0.08 grams of alcohol in 100 $cm^3$ of blood are being considered. The more challenging 0.08 grams of alcohol in 100 $cm^3$ of blood is used to determine the practicality of the ILS techniques described herein. A well-established aliquot part of the blood alcohol concentration is present in the breath of an individual after the consumption of alcohol. For the purpose of converting between breath alcohol content and blood alcohol content, a factor of 2100 is widely accepted, supra. Utilizing this conversion factor, 0.08 grams of alcohol in 100 $cm^3$ blood result in an alcohol concentration of $2 \times 10^{-2}$ $cm^3$ per 100 $cm^3$ breath or $2 \times 10^{-4}$ $cm^3$ alcohol per 1 $cm^3$ breath.

Figure 1:
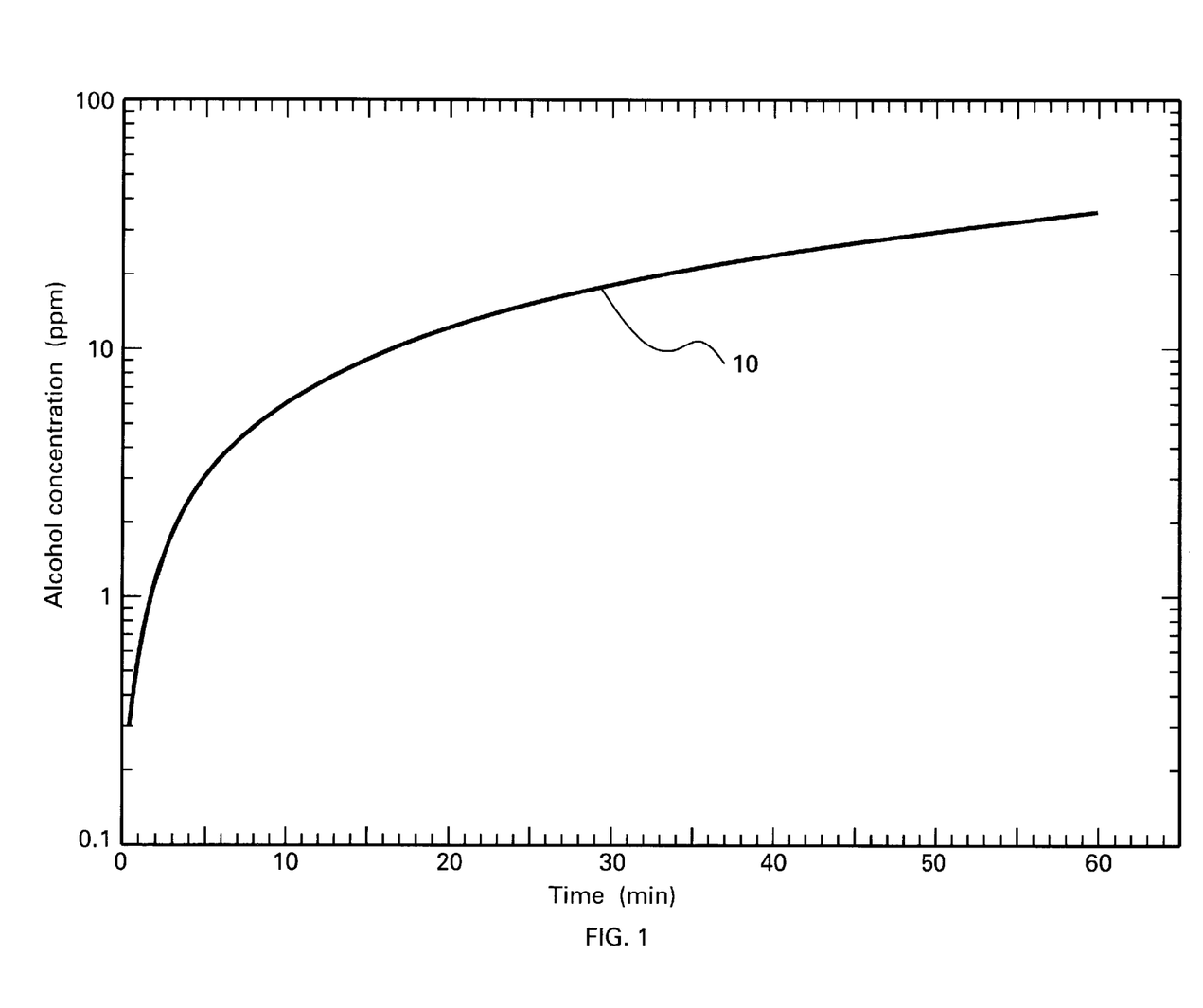
FIG. 1, on coordinates of concentration (in ppm) and time (in minutes), is a plot of alcohol generation in a closed vehicle cabin.

Assuming a breathing rate of 15 times per minute with an average breath volume of 500 $cm^3$, then the volume of alcohol generated per minute inside a closed vehicle cabin, based on single occupancy, can be calculated to be:

$$2 \times 10^{-4} \text{ cm}^3 \cdot 500 \cdot 15 = 1.5 \text{ cm}^3/\text{minute}.$$

Assuming further the volume of a vehicle to be 2.5 $m^3$, then the concentration of alcohol in a car with windows closed increases steadily and reaches a concentration in the parts per million (ppm) range within minutes. Curve 10 of FIG. 1, which is a plot of the concentration of alcohol (in ppm) as a function of time (in minutes), illustrates this calculation. Curve 10 is based on a temperature of 20° C., a pressure of 760 Torr, and single occupancy in the vehicle.

A separate study by Science Application International Corporation (SAIC) discussed in U.S. Pat. No. 5,349,187, issued Sep. 20, 1994, to Ali Dabiri et al concludes that the alcohol concentration in the vehicle exceeds 3 ppm after 30 minutes under similar conditions when all windows are closed and no ventilation is turned on.

The same disclosure by SAIC found the alcohol concentration to be much lower in the case of windows fully opened and fresh air supplied by the ventilation. Although sub-ppm alcohol concentrations in the vehicle cabin have to be assumed in the case of high air exchange rates, the alcohol concentration in the vicinity of the driver is much higher and can be estimated to reach ppm levels, if not higher. Considering the fact that small on-board sensors can be placed in close proximity to the location of the highest alcohol concentration (i.e., next to the driver's head), high air exchange rates are not expected to present a particular challenge for on-board ILS alcohol sensors.

Choosing the appropriate spectral region for alcohol detection is critical to achieve high sensitivity and to avoid interference with other airborne species present in a vehicle. At the same time, operational limitations of ILS laser and signal detector have to be considered and lead to a restriction of the usable wavelength regions.

Taking these considerations into account, a wavelength range from 1 to 4 μm was selected for a detailed analysis. The following sources for absorption spectra were used: data obtained by Sadtler Research Laboratories (Sadtler Research Laboratories, Inc. Philadelphia, Spectra work book, Editor: A. R. Gennaro, 1966–1968), U.S. Pat. No. 5,349,187 (supra, and Fang et al (H. L. Fang et al, "Molecular conformers in gas-phase ethanol: a temperature study of vibrational overtones", Chemical Physics Letters, Vol. 105, pp. 5–11, 1984).

Figure 2:
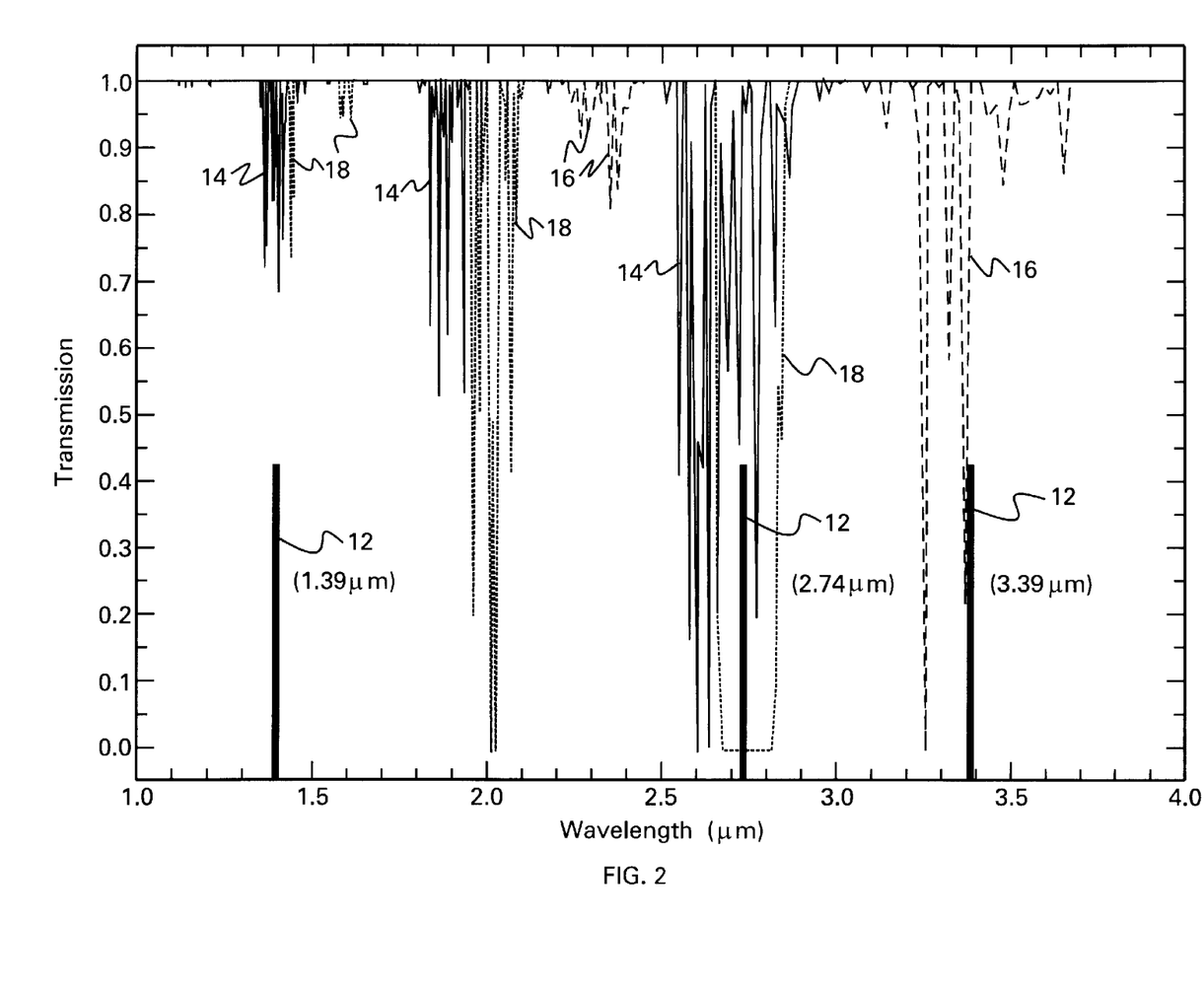
FIG. 2, on coordinates of transmission and wavelength (in $\mu$m), is a plot of alcohol absorption between 1 and 4 $\mu$m, showing also absorption of water ($H_2O$), methane ($CH_4$), and carbon dioxide ($CO_2$) in the same range, which are examples of other gaseous species found in air that might be considered as spectral interferents.

The spectrum measured by Sadtler Research Laboratories shows two absorption peaks at 3.0 μm and 3.39 μm. In the spectrum reported by SAIC, absorption peaks appear at 1.5 μm, 2.74 μm, and 3.39 μm. No absorption feature is observed at 3.0 μm in this spectrum, however. According to results presented by Fang et al., two pronounced alcohol absorption features exist at 1.3998 μm and 1.3928 μm. FIG. 2 summarizes prominent absorption regions of alcohol between 1 μm and 4 μm, as well as absorption features of other molecules absorbing in this wavelength region. The alcohol absorption wavelengths are denoted at 12 (1.39 μm, 2.74 μm, and 3.39 μm). The absorption of water is indicated by Curve 14, the absorption of methane by Curve 16, and the absorption of carbon dioxide by Curve 18. Water absorption features in the vicinity of 1.39 μm are displayed with higher resolution in FIG. 3.

The absorption coefficient of alcohol at 1.39 μm was determined by H. L. Fang et al, supra, to be approximately 0.12 cm$^{-1}$ atm$^{-1}$, corresponding to an absorption cross section of 4.9×10$^{-2}$ cm$^2$. An absorption coefficient of 4.27 cm$^{-1}$ atm$^{-1}$, corresponding to an absorption cross section of 1.7×10$^{19}$ cm$^2$ was reported for alcohol absorption at 3.39 μm.

The ability to detect molecules with absorption cross sections similar to the absorption cross section calculated for alcohol has been previously demonstrated successfully by the inventors for various molecules in the parts per million (ppm) and parts per billion (ppb) concentration range. The following Table I summarizes results achieved for different species:

TABLE I

Absorption cross section of alcohol and various molecules successfully detected with ILS instrumentation.

| Molecule | Absorption Cross Section [cm$^2$] |
|---|---|
| H$_2$O | 8.20 × 10$^{-21}$ |
| CO$_2$ | 5.40 × 10$^{-21}$ |
| NH$_3$ | 22.0 × 10$^{-21}$ |
| CH$_3$CH$_2$OH | 4.9 × 10$^{-21}$ |

The comparison given in Table I clearly demonstrates the ability of ILS alcohol sensors to detect alcohol vapor even when assuming sub-ppm alcohol levels inside a vehicle in the worst case of high air flow through open windows and additional high ventilation air flow. Taking into account the presumably much higher alcohol concentration in the vicinity of the driver, detecting alcohol impaired vehicle operators with ILS alcohol sensors is a highly promising approach.

Figure 4:
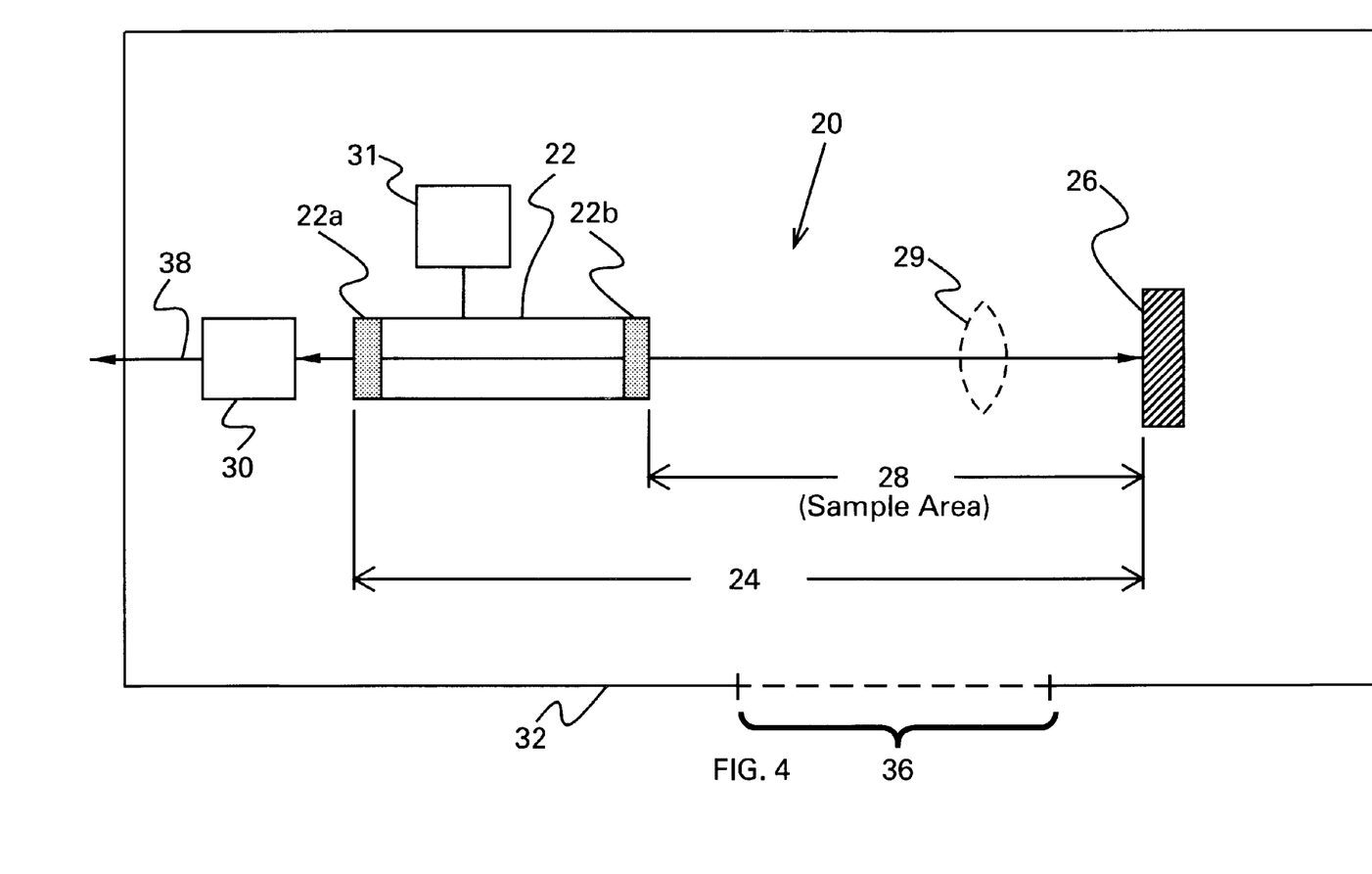
FIG. 4 is a schematic diagram of an on-board ethyl alcohol sensor of the present invention, comprising a diode laser with an external cavity.

An example of on-board alcohol sensor in accordance with the present invention and based on a multi-mode diode laser with an external cavity is now described. This approach has been studied in detail experimentally and theoretically for its applicability to ILS measurements and complies with requirements outlined in previous paragraphs. The sensor 20, which is configured to detect ethyl alcohol vapors to a sensitivity of ppm or lower, is shown in FIG. 4. Although one specific embodiment is depicted, other configurations of the basic sensor may also be constructed, based on the teachings herein.

In a laser 22 functioning as an intracavity spectroscopic device, a broadband laser resonator 24 is established between a first facet 22a of the laser diode, or gain medium, and a highly reflective end mirror 26. The first facet 22a is provided with a reflectivity coating to effectively utilize the gain of the laser medium to achieve threshold for laser action. A second facet 22b facing the end mirror 26 is preferably anti-reflection coated in order to provide the highest transmission possible and to minimize interference effects. An external cavity region (i.e., sample area) 28 where alcohol molecules are present is established between the end mirror 26 and the antireflection coated facet 22b of the laser diode 22. An optical element 29, for example, a lens, may be placed inside the cavity to focus, expand, or collimate light emitted from the internal facet onto the end mirror and the reflected light back into the diode. In this configuration, the external cavity region of the laser resonator itself can be used as the sample cell 28, and the entire assembly 20, with or without a detector 30 (described below) is mounted in a small container or housing 32. The alcohol molecules enter the sample area 28 through an input port 36.

Preferably, the laser 22 is a solid-state laser, for example, a diode laser, for compactness and relatively low power consumption. The laser 22 may be an external cavity diode laser (ECDL) or a superluminescent diode (SLD) laser, for example, and may be driven either electrically or optically (e.g., a second laser or lamp), as shown at 31.

A suitable detector (e.g., a photodiode sensitive to the detection wavelength selected) 30 is mounted next to the first facet 22a of the laser diode 22 and responds to changes in laser intensity, laser wavelength, and/or laser temporal properties altered by changing alcohol concentrations. The detector 30 provides an output signal 38 that is subsequently employed to provide an indication of threshold alcohol concentration, as described more fully below. Examples of suitable photodiodes include germanium and (In,Ga)As.

With a similar experimental setup, an absorption coefficient of 10$^{-6}$ cm$^{-1}$ has been measured for a rubidium transition in a heat pipe at 780 nm (V. M. Baev et al, Applied Physics, vol. B55, pp. 463–477, 1992). The absorption coefficient for alcohol has been calculated by the present inventors to be 1.2×10$^{-7}$ cm$^{-1}$. Thus, alcohol detection by ECDL/ILS appears to be readily achievable.

In principle, alcohol detection in the 1 μm to 4 μm region utilizing on-board ILS sensor systems can be conducted at 1.39 μm, 2.74 μm or 3.39 μm where alcohol molecules show absorption features (see FIG. 2). Only 1.39 μm and 3.39 μm, however, are useful under conditions encountered in vehicles, since alcohol absorption at 2.74 μm is heavily masked by strong CO$_2$ absorption bands (CO$_2$ is a normal component of exhalation).

Possible interference with alcohol measurements at 1.39 μm could result from ambient moisture present in the vehicle. A close examination of literature database absorption, however, reveals distinctive absorption voids in the water absorption spectrum around 1.39 μm, possibly allowing for alcohol detection at this wavelength. (L. S. Rothman, The Hitran Molecular Database. J. Quant. Spectrosc. Radiat. Transf., Vol. 48, pp. 5/6, 1992).

Figure 3:
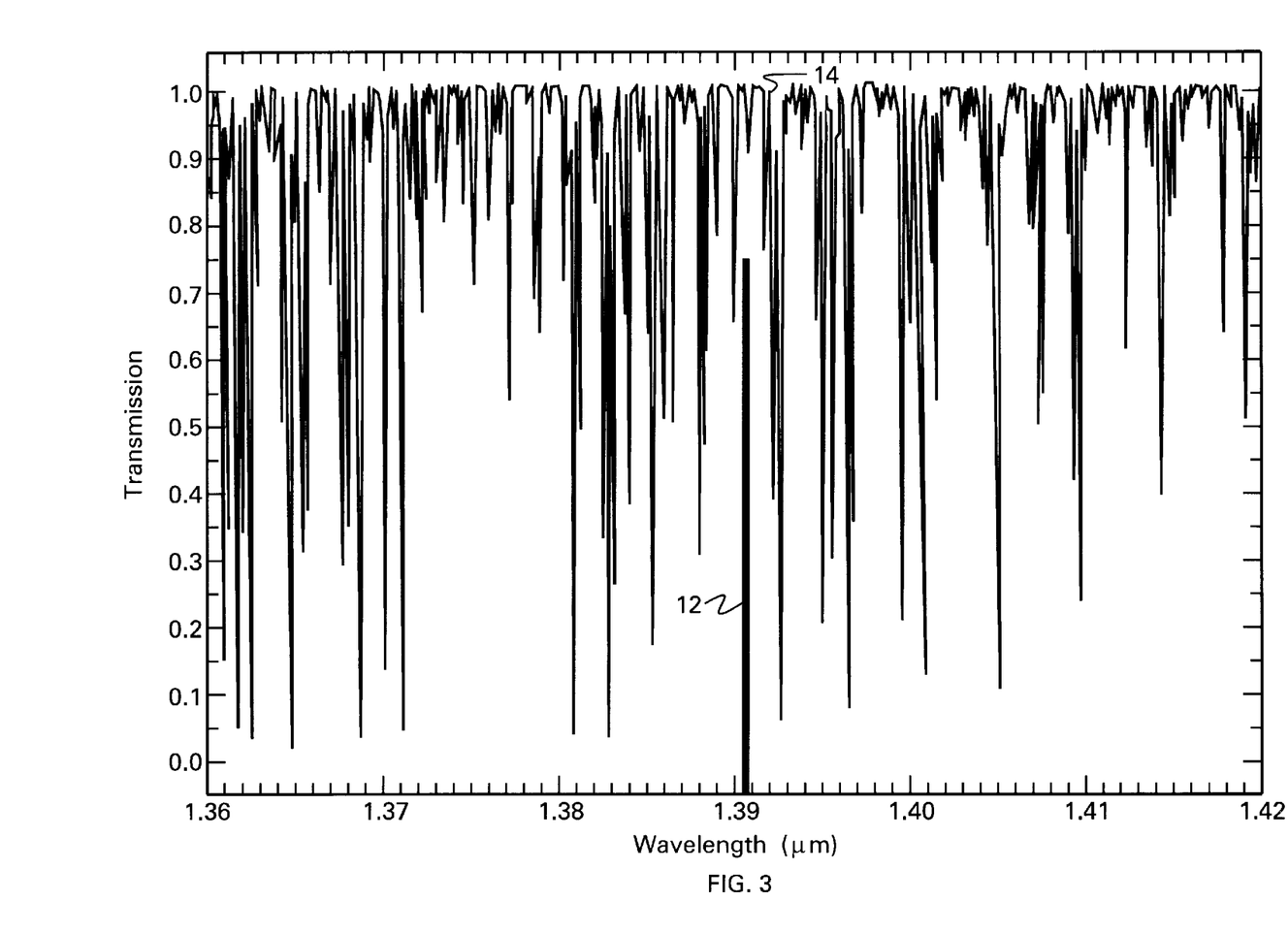
FIG. 3, on coordinates of transmission and wavelength (in $\mu$m), is a plot of alcohol absorption around 1.39 $\mu$m.

Therefore, ambient moisture absorption is not expected to present a problem for alcohol detection with an on-board ILS alcohol sensor. No other molecular species present during the normal operation of a vehicle would cause a significant response of an on-board alcohol sensor working in at this wavelength. FIG. 3 shows a high resolution view of this spectral region.

Alcohol absorption at 3.39 μm can possibly be disturbed by methane ($CH_4$) generated by the car engine. No other molecular species present inside a vehicle cabin shows absorption features in the same spectral region.

Since the on-board alcohol sensor 20 is completely enclosing the laser beam, its use totally obviates any laser radiation damage concerns, since the radiation is contained within the sensor housing 32. Furthermore, the wavelength-laser energy combination to be utilized was identified to be within the so-called "eye safe region" so as to present no potential danger to eyes and skin of people occupying the vehicle. It meets emission limit requirements for Class 1 laser systems, which are considered to be safe for humans. In detail, Class 1 laser systems are defined as follows (U.S. Department of Health and Human Services, Public Health Service, Food and Drug Administration, "Regulation for the Administration and Enforcement of the Radiation Control for the Health and Safety Act of 1968", Code of Federal Regulations, Parts 1000 to 1005, 1996):

"Class 1 laser product means any laser product that does not permit access during the operation to levels of laser radiation in excess of the accessible emission limits. Class 1 levels of laser radiation are not considered to be hazardous."

Figure 5:
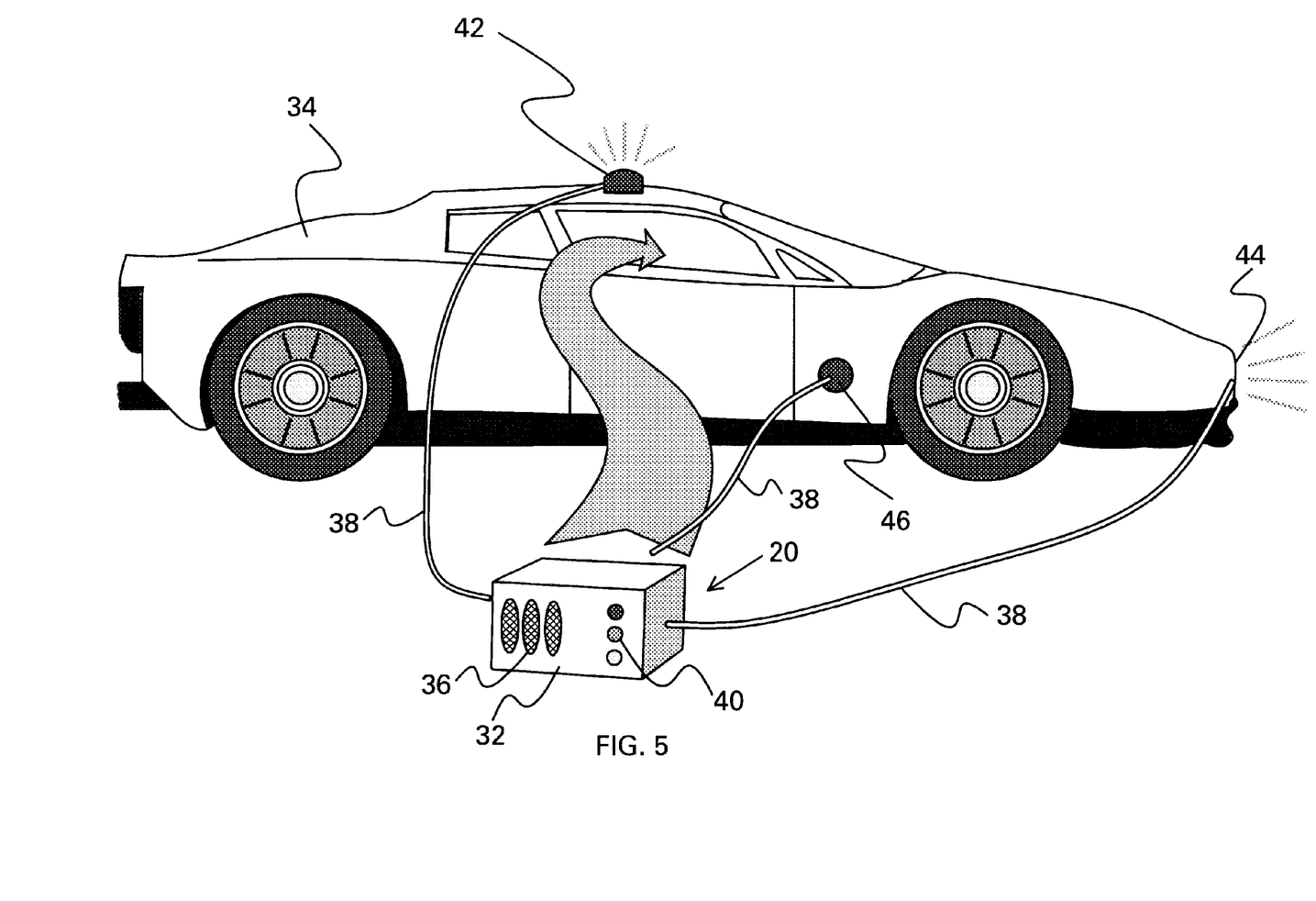
FIG. 5 is a schematic diagram of incorporation of the on-board alcohol sensor of the present invention in a vehicle, illustrating activation of various internal indicators.

FIG. 5 illustrates several implementations and applications of an on-board ILS alcohol sensor 20 in a vehicle 34. The housing 32 is provided with a cabin air intake 36, which admits air from the cabin of the vehicle 34 for introduction into the sample area 28 of the sensor 20. The air may enter the sample area 28 by simple diffusion or by use of an active device, such as a fan (not shown) that pushes or pulls air into the sample area.

There are a variety of applications to which a signal 38 from the detector 30 can be directed. These applications include, but are not limited to, (1) internal warning signals, such as a light display 40, perhaps mounted on the housing 32, for alerting the vehicle occupant(s), (2) visible external indicators, such as a flashing light 42 mounted on the vehicle 34 or direct connection from the detector 30 to headlights 44 to cause them to flash, and (3) invisible external indicators (e.g., infrared) warning lights 46 to be detected by the police only or by a remote test station, or by a satellite.

For example, a suitably configured "alcohol gun" (i.e., configured to detect the output signal 38) aimed at the external indicator 46 could provide the police with a measure of the alcohol concentration inside the vehicle cabin. Or, test stations, periodically established along a highway, could be configured to sense each vehicle as it passes, "interrogating" the vehicle to determine the alcohol concentration therein. Or, in a more sophisticated system, a radio signal could be sent to a satellite and retransmitted to a suitable ground receiving station to provide a measure of the alcohol concentration inside the vehicle.

Figure 6A:
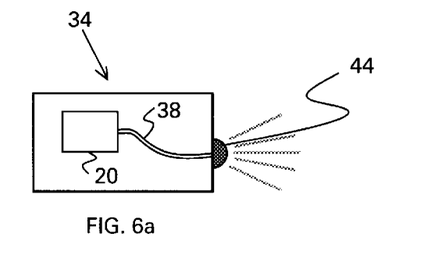
FIGS. 6a–6d are schematic illustrations, depicting four alternate embodiments for emitting a signal representative of alcohol concentration information to law enforcement personnel by various external indicators, including flashing headlights of the vehicle (FIG. 6a), an "alcohol gun" (FIG. 6b), a permanent roadside alcohol detector (FIG. 6c), and a satellite detector for transmission to mobile and/or stationary law enforcement (FIG. 6d).

FIGS. 6a–6d schematically depict various external indicators. FIG. 6a illustrates connection of the on-board ILS sensor 20 to flashing headlights 44 via output signal 38, to enable visual detection of alcohol concentration by conventional vehicular instrumentation.

Figure 6B:
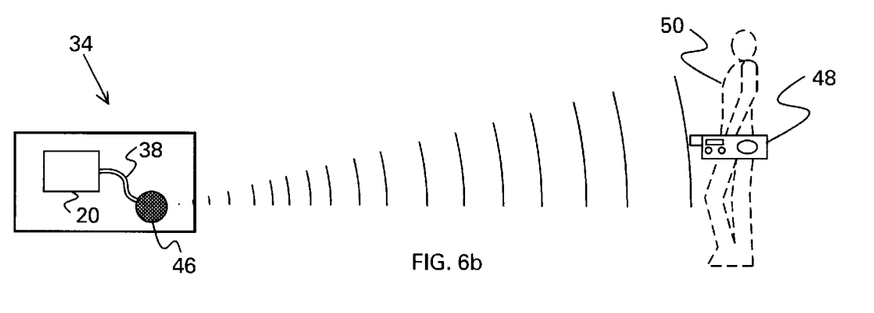

FIG. 6b illustrates connection of the on-board ILS sensor 20 to signal emitter 46 via output signal 38, to enable detection of alcohol concentration by an "alcohol gun" 48 operated by law enforcement personnel 50. The alcohol gun 48 is configured to detect the emitted signal and translate it into alcohol concentration, much like a radar gun is configured to translate motion of a vehicle into speed.

Figure 6C:
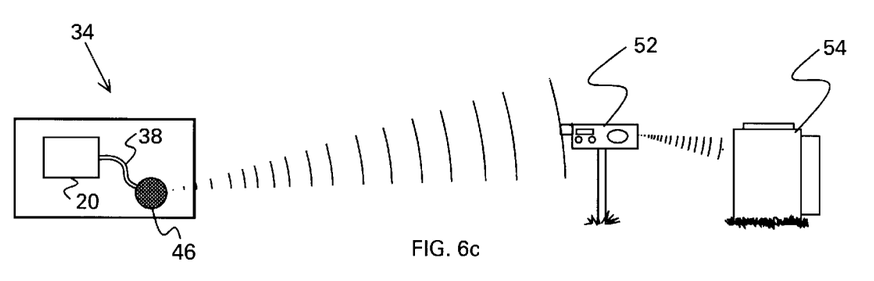

FIG. 6c illustrates connection of the on-board ILS sensor 20 to signal emitter 46 via output signal 38, to enable detection of alcohol concentration by a permanently placed roadside detector 52, which then transmits the information received to mobile and/or stationary law enforcement 54. The roadside detector 52 is configured much like the alcohol gun 48, and includes additional components for transmission of the information.

Figure 6D:
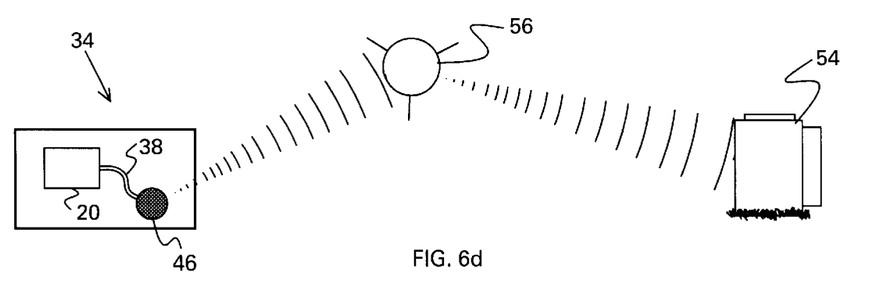

FIG. 6d illustrates connection of the of the on-board ILS sensor 20 to signal emitter 46 via output signal 38, to enable detection of alcohol concentration by a satellite 56, which then transmits the information received to mobile and/or stationary law enforcement 54. The satellite 56 is configured much like the roadside detector 52.

INDUSTRIAL APPLICABILITY

The on-board ethyl alcohol sensor of the present invention is expected to find use in vehicles to provide drivers and law enforcement officials with an indication of any alcohol vapors inside the vehicle cabin resulting from exhalation by intoxicated drivers.

Thus, there has been disclosed an on-board ethyl alcohol sensor for detection of ethanol vapors in vehicular cabins. It will be readily appreciated by those skilled in this art that various changes and modifications of an obvious nature may be made, and all such changes and modifications are considered to fall within the scope of the invention, as defined by the appended claims.

What is claimed is:

1. An on-board ILS sensor for detecting the presence of ethyl alcohol vapors in a cabin of a vehicle, comprising:

(a) a laser comprising a gain medium having two opposed facets within a laser resonator and functioning as an intracavity spectroscopic device having a first end and a second end, said first end operatively associated with a partially reflecting surface;

(b) a reflective or dispersive optical element operatively associated with said second end to define a broadband wavelength laser resonator between said optical element and said first end and to thereby define an external cavity region between at least one facet of said gain medium and either said first end or said second end or both ends;

(c) said external cavity region being exposed to air in said cabin of said vehicle to enable any ethyl alcohol molecules to enter thereinto;

(d) a detector spaced from said first end and providing an output detector signal;

(e) electronic means for measuring and analyzing said detector signal;

(f) a housing for containing at least said laser, said partially reflecting surface, and said optical element, said housing being configured to prevent escape of stray radiation into said cab and to permit air from said cab to continuously circulate through said external cavity region for analysis; and (g) means for driving said laser.

2. The on-board ILS sensor of claim 1 wherein said gain medium has an antireflective coating to maximize transmission and minimize interference effects.

3. The on-board ILS sensor of claim 1 wherein said first end has a reflectivity to effectively utilize the gain of the laser medium to achieve threshold for laser action.

4. The on-board ILS sensor of claim 1 wherein said reflective or dispersive optical element comprises a mirror or a diffraction grating, respectively.

5. The on-board ILS sensor of claim 1 wherein said detector comprises a photodiode sensitive to a selected wavelength related to an absorption frequency of said ethyl alcohol.

6. The on-board ILS sensor of claim 5 wherein said wavelength is within a range of about 1 to 4 $\mu$m.

7. The on-board ILS sensor of claim 6 wherein said wavelength is selected from the group 1.39, 2.74, and 3.39 $\mu$m.

8. The on-board ILS sensor of claim 1 wherein said detector is operatively associated with an internal indicator.

9. The on-board ILS sensor of claim 1 wherein said detector is operatively associated with an external indicator.

10. The on-board ILS sensor of claim 9 wherein said external indicator is a light mounted on said vehicle.

11. The on-board ILS sensor of claim 9 wherein said external indicator is accessible by a portable sensor or a remote test station or transmits a signal to a satellite.

12. The on-board ILS sensor of claim 1, wherein said detector is capable of detecting ethyl alcohol in a concentration of at least 1 part per million.

13. The on-board ILS sensor of claim 1 wherein said laser is selected from the group consisting of external cavity diode lasers and superluminescent diode lasers.

14. The on-board ILS sensor of claim 1, wherein said detector comprises a photodiode.

15. A method for measuring concentration of ethyl alcohol vapors representative of air in a cabin in a vehicle employing an on-board ILS sensor comprising
 (a) a laser comprising a gain medium having two opposed facets within a laser resonator and functioning as an intracavity spectroscopic device having a first end and a second end, said first end operatively associated with a partially reflecting surface;
 (b) a reflective or dispersive optical element operatively associated with said second end to define a broadband wavelength laser resonator between said optical element and said first end and to thereby define an external cavity region between at least one facet of said gain medium and either said first end or said second end or both ends;
 (c) said external cavity region being exposed to air in said cabin of said vehicle to enable any ethyl alcohol molecules to enter thereinto;
 (d) a detector spaced from said first end;
 (e) electronic means for measuring and analyzing said detector signal;
 (f) a housing for containing at least said laser, said partially reflecting surface, and said optical element, said housing being configured to prevent escape of stray radiation into said cab and to permit air from said cab to continuously circulate through said external cavity region for analysis; and
 (g) means for driving said laser, said method comprising:
  (1) sensing any said ethyl alcohol vapors representative of air in said cabin by said on-board ILS sensor; and
  (2) providing a signal indicative of presence of any said alcohol vapors.

16. The method of claim 15 wherein said signal is internal to said vehicle and provides a warning to an occupant of said vehicle.

17. The method of claim 15 wherein said signal is external to said vehicle.

18. The method of claim 17 wherein said signal activates an external indicator comprising a light mounted on said vehicle.

19. The method of claim 17 wherein said signal activates an external indicator that is accessible by a portable sensor or a remote test station or transmits a signal to a satellite.

20. The method of claim 15 wherein said detector is capable of detecting ethyl alcohol in a concentration of at least 1 part per million.

* * * * *